(12) United States Patent
Rigneault et al.

(10) Patent No.: US 11,428,924 B2
(45) Date of Patent: Aug. 30, 2022

(54) DEVICES AND METHODS FOR CONVEYING AND CONTROLLING LIGHT BEAMS FOR LENSLESS ENDO-MICROSCOPIC IMAGERY

(71) Applicants: CENTRE NATIONAL DE LA RECHERCHE SCIENTIFIQUE—CNRS, Paris (FR); Universite d'Aix-Marseille (AMU), Marseilles (FR); Ecole Centrale de Marseille (ECM), Marseilles (FR)

(72) Inventors: Hervé Rigneault, Allauch (FR); Esben Ravn Andresen, Lille (FR); Siddarth Sivankutty, Marseilles (FR)

(73) Assignees: CENTRE NATIONAL DE LA RECHERCHE SCIENTIFIQUE—CNRS, Paris (FR); Ecole Centrale de Marseille (ECM), Marseilles (FR); Université d'Aix-Marseille (AMU), Marseilles (FR)

( * ) Notice: Subject to any disclaimer, the term of this patent is extended or adjusted under 35 U.S.C. 154(b) by 478 days.

(21) Appl. No.: 16/091,200

(22) PCT Filed: Apr. 4, 2017

(86) PCT No.: PCT/EP2017/058017
§ 371 (c)(1),
(2) Date: Sep. 21, 2020

(87) PCT Pub. No.: WO2017/174596
PCT Pub. Date: Oct. 12, 2017

(65) Prior Publication Data
US 2021/0018744 A1    Jan. 21, 2021

(30) Foreign Application Priority Data
Apr. 4, 2016  (FR) ...................... 1652937

(51) Int. Cl.
*G02B 23/24* (2006.01)
*G02B 6/02* (2006.01)
(Continued)

(52) U.S. Cl.
CPC ........ *G02B 23/2469* (2013.01); *A61B 1/0017* (2013.01); *A61B 1/00167* (2013.01);
(Continued)

(58) Field of Classification Search
CPC ............ G02B 6/02042; G02B 23/2469; G02B 23/2423; G02B 27/0087; G02B 6/262;
(Continued)

(56) References Cited

U.S. PATENT DOCUMENTS

| 8,585,587 B2 | 11/2013 | French et al. |
| 2002/0190212 A1* | 12/2002 | Boas ................... A61B 5/0068 250/341.1 |

(Continued)

FOREIGN PATENT DOCUMENTS

| CN | 204 405 899 U | 6/2015 | |
| CN | 204405899 U * | 6/2015 | ............... G02B 6/40 |

(Continued)

OTHER PUBLICATIONS

E. R. Andresen et al; "Measurement and compensation of residual group delay in a multi-core fiber for lensless endoscopy"; Journal of the Optical Society of America, vol. 32, No. 6, pp. 1221-1228; Jun. 2015 (8 pages).

(Continued)

*Primary Examiner* — Michael P Mooney
(74) *Attorney, Agent, or Firm* — Osha Bergman Watanabe & Burton LLP

(57) ABSTRACT

According to one aspect, the invention relates to a device for transporting and controlling light beams for endo-microscopic imaging without a lens on the distal side comprising (Continued)

a single-mode optical fibre bundle (40) on the distal side, wherein each single-mode optical fibre is intended to receive an elementary light source and to emit a light beam at a distal end; a single-mode optical fibre section (50) arranged at the distal end of the optical fibre bundle and intended to receive the light beams emitted by the single-mode optical fibres of the optical fibre bundle; an optical phase control device arranged on the side of the proximal end of the single-mode optical fibres. The optical phase control device comprises at least one spatial light modulator (30) adapted to apply a phase shift to each of the elementary beams and control means (60) for controlling the spatial light modulator allowing application of a phase shift to each of the elementary beams to form an illumination beam with a determined phase function at the distal end of the multimode optical fibre section (50).

10 Claims, 7 Drawing Sheets

(51) Int. Cl.
*A61B 1/00* (2006.01)
*A61B 1/07* (2006.01)
*G02B 27/00* (2006.01)

(52) U.S. Cl.
CPC ..... *G02B 6/02042* (2013.01); *G02B 23/2423* (2013.01); *A61B 1/00172* (2013.01); *A61B 1/07* (2013.01); *G02B 27/0087* (2013.01)

(58) Field of Classification Search
CPC ....... A61B 1/07; A61B 1/0669; A61B 1/0017; A61B 1/00167; A61B 1/00172
USPC .................................................. 385/50, 117
See application file for complete search history.

(56) References Cited

U.S. PATENT DOCUMENTS

| 2011/0137126 A1 | 6/2011 | French et al. |
| 2016/0022119 A1 | 1/2016 | Shahmoon et al. |

FOREIGN PATENT DOCUMENTS

| JP | 2008-506426 A | 3/2008 |
| JP | 2009-22729 A | 2/2009 |
| JP | 2011-527218 A | 10/2011 |
| WO | 2006/014392 A1 | 2/2006 |
| WO | 2007/084849 A1 | 7/2007 |

OTHER PUBLICATIONS

E. R. Anderson et al; "Two-photon lensless endoscope"; Optical Express, vol. 21, No. 18, pp. 20713-20721; Sep. 9, 2013 (9 pages).
E. R. Anderson et al; "Toward endoscopes with No. distal optics: video-rate scanning microscopy through a fiber bundle"; Optical Letters, vol. 38, No. 5, pp. 609-611; Mar. 1, 2013 (3 pages).
T. A. Birks et al; "The photonic lantern"; Advances in Optics and Photonics 7, pp. 107-167; 2015 (61 pages).
T. Cizmar et al; "Exploiting multimode waveguides for pure fibre-based imaging"; Nature Communications, vol. 3, No. 1027, pp. 1-9; 2012 (9 pages).
T. Cizmar et al; "Shaping the light transmission through a multimode optical fibre: complex transformation analysis and applications in biophotonics"; Optical Express, vol. 19, No. 20, pp. 18871-18884; Sep. 26, 2011 (14 pages).
International Search Report issued in PCT/EP2017/058017 dated Jul. 7, 2017 (6 pages).
Written Opinion of the International Searching Authority issued in PCT/EP2017/058017 dated Jul. 7, 2017 (8 pages).
Notice of Reasons for Rejection issued in Japanese Application No. 2019-502158, dated Dec. 1, 2020 (4 pages).

\* cited by examiner

DEVICES AND METHODS FOR CONVEYING AND CONTROLLING LIGHT BEAMS FOR LENSLESS ENDO-MICROSCOPIC IMAGERY

STATE OF THE ART

Technical Field of the Invention

The present invention relates to devices and methods for transporting and controlling light beams for so-called "lensless" endo-microscopic imaging in addition to lensless endo-microscopic imaging systems and methods. It applies in particular to endoscopic exploration of organs in a living being, either human or animal.

State of the Art

Developments in endo-microscopic imaging call for use of opto-mechanical fibre devices having specific characteristics compared to free-space imaging systems.

Indeed, building a miniature microscope that would comprise a light source, a focusing optic and a camera at the distal end (i.e. located at the end of the fibre, on the sample side) of a medical endoscope is not conceivable owing to the overall dimensions of the entire components. Consequently, solutions are sought that allow performance of imaging at the end of the optical fibre while limiting the overall dimensions at the distal end of the endoscope.

Several approaches exist that allow performance of imaging at the end of the optical fibre while limiting the overall dimensions at the distal end of the endoscope.

In particular, technology termed "lensless endoscopy" is known, described for example in Cizmar et al. "Exploiting multimode waveguides for pure fibre-based imaging", Nat. Commun. 3, 1027 (2012). This method is based on using a multimode fibre, or MMF. The MMF optical fibre is illuminated with a coherent source. On the proximal side (i.e. at the optical fibre input, on the side opposite the sample) of the MMF optical fibre, a spatial light modulator, SLM, makes it possible to vary the propagation modes of the fibre in such a way that the coherent addition of these modes allows generation of the desired intensity figure at the end of the MMF fibre. In one embodiment, it is attempted for example to produce a focal point at the end of the MMF fibre and scan the sample to obtain an image as would be done in a conventional confocal microscopy assembly.

This method, which is extremely powerful owing to the deterministic nature of the fibre transmission matrix which connects an input field at the proximal portion of the fibre with an output field at the distal portion (and vice versa) makes it possible to dispense with any optics on the distal side of the multimode fibre and thus reduce overall dimensions.

The fibre transmission matrix is however heavily dependent on the curvature of the MMF optical fibre. Endo-microscopic imaging using an MMF optical fibre is therefore highly sensitive to any movement of the fibre. Furthermore, owing to the multimode nature, a short pulse in the proximal portion is prolonged in the distal portion, which restricts the possible applications to non-linear imaging that requires working with light pulses of high peak intensities.

Alongside technologies based on use of multimode fibres, a "lensless"-type technology has also developed, based on use of a single-mode optical fibre bundle (see for example French et al. U.S. Pat. No. 8,585,587). According to the technique described, a spatial light modulator (SLM) arranged on the proximal side of the single-mode optical fibre bundle serves to control the wavefront emitted by the light source at the distal end of the fibre bundle. This technique is much less sensitive to movement, especially twisting of the optical fibre bundle. Indeed, since the modes of the single-mode optical fibres are localised and confined to specific points on the transverse surface of the optical fibre bundle, twisting of the optical fibre bundle results in mere translation of the intensity figure. Furthermore, the single-mode nature of the fibres eliminates any intermodal dispersion; thus, the only contribution to dispersion is chromatic dispersion, which is the same for all single-mode optical fibres and can therefore be compensated globally. Consequently, use of a single-mode optical fibre bundle allows, in comparison to multimode fibres, propagation of short pulses.

Various publications have described alternative embodiments of lensless endo-microscopy based on use of a single-mode optical fibre bundle and more specifically, a multi-core fibre or MCF. Thus, for example, it is shown how very rapid scanning of the focal point can be achieved in the distal portion of the optical fibre bundle by imparting a variable angle of the wavefront at the SLM input with a galvano-metric device (see for example E. R. Andresen et al. "Toward endoscopes with no distal optics: video-rate scanning microscopy through a fibre bundle", Opt. Lett. Vol. 38, N° 5, 609-611 (2013)). In E. R. Andresen et al. ("Two-photon lensless endoscope», Opt. Express 21, N° 18, 20713-20721 (2013)), the authors demonstrated the experimental feasibility of a two-photon non-linear imaging (TPEF) system in lensless endo-microscopy. E. R. Andresen et al. ("Measurement and compensation of residual group delay in a multi-core fibre for lensless endoscopy", JOSA B, Vol. 32, No. 6, 1221-1228 (2015)), describes a group delay control, GDC, device for transporting and controlling light pulses in a lensless endo-microscopic imaging system based on use of a single-mode optical fibre bundle.

FIG. 1A diagrammatically depicts a lensless endo-microscopic imaging system 100 using a single-mode optical fibre bundle. The imaging system 100 typically comprises an emission source 10 for emitting an incident light beam $B_0$, either continuous or in pulse form in the case of application to non-linear imaging. The system 100 also includes a detection channel comprising a lens 21 and a detector 20. The detection channel is separated from the emission channel by a beam splitter 22. The imaging system 100 also comprises a device for transporting and controlling the light beams allowing illumination of a remote analysis object 101. The transport and control device comprises a single-mode optical fibre bundle 40, the input facet (or proximal facet) 41 and output facet (or distal facet) 42 of which are shown enlarged in FIG. 1A and a spatial light modulator (SLM) 30 arranged at the proximal end of the fibre bundle 40 serving to control the wavefront of the beam emitted by the source 10. The spatial light modulator imparts to the incoming wave front, having a phase function $\Phi_0$, a given phase shift $\Phi_1(i)$ for each elementary beam $B_i$ intended to enter an optical fibre $F_i$ of the fibre bundle 40. The phase function $\Phi_1(i)$ may be such that, for example, following propagation in the optical fibre bundle, the wave emerges with a parabolic phase $\Phi_2(i)$. This parabolic phase allows the beam to focus on the analysis object 101 on the distal side, whereas no physical lens is present; this is the origin of the term "lensless endoscopy". Furthermore, the spatial light modular allows compensation of the phase shifts introduced by each of the optical fibres $F_i$.

The bundle of N single-mode optical fibres can be formed of a set of individual single-mode optical fibres, each comprising a core and a cladding, typically a hundred to a few tens of thousands of fibres, grouped in the form of a bundle of fibres; the bundle of N single-mode optical fibres may also consist of a set of single-mode cores of a multi-core fibre, preferably at least a hundred single-mode cores, as shown in FIG. 1B. Thus, the example in FIG. 1B illustrates a multi-core fibre 40 that comprises a set of single-mode cores $F_i$, an external cladding 43 and also in this example, a multimode internal cladding 44 adapted to collect the light signal backscattered by the analysis object from the distal end to the proximal end.

In most cases, for matters relating to the manufacturing process of the optical fibre bundle, whether in the case of a bundle formed of a set of single-mode fibres or a set of single-mode cores of a multi-core fibre, the single-mode fibres are arranged periodically or virtually periodically within the fibre bundle.

In the case of periodic or virtually periodic arrangement of the cores, the applicants have shown that a wave with a parabolic phase $\Phi_2(i)$ will result in a given image plane, not in a single image point but rather, as is shown as the FIG. 1C in a bright luminous central point ($P_1$) surrounded by luminous points of lesser intensity ($R_i$), known as "replicas". This effect results directly from the periodicity or virtual periodicity of the arrangement of optical fibres in the fibre bundle, which behaves like a diffraction grating, with the replicas resulting from diffraction higher orders of the wave propagating through the optical fibre bundle.

The present invention provides devices and methods for transporting and controlling light beams for so-called "lensless" endo-microscopic imaging systems that make it possible to dispense with the replicas in the image plane, regardless of the arrangement of the optical fibres within the optical fibre bundle.

SUMMARY OF THE INVENTION

According to a first aspect, the present description relates to a device for transporting and controlling light beams for "lensless" endo-microscopic imaging, i.e. without a lens on the distal side, comprising:
- a first light guide comprising a single-mode optical fibre bundle, wherein each single-mode optical fibre is intended to receive an elementary light beam at a proximal end and emit a light beam at a distal end,
- a second light guide comprising a multimode optical fibre section, arranged at the distal end of the first light guide, wherein the multimode optical fibre section is intended to receive the light beams emitted by the single-mode optical fibres of the single-mode optical fibre bundle;
- an optical device for phase control arranged on the side of the proximal end of the first light guide comprising:
  - at least one spatial light modulator adapted to apply a phase shift to each of the elementary beams;
  - means of controlling the first spatial light modulator allowing application of a phase shift to each of the elementary beams in order to form an illumination beam with a determined phase function at the distal end of the multimode optical fibre section.

The applicants have shown that a device for transporting and controlling light beams thus described allows transport of light beams over long distances, typically greater than 100 cm, with no consequences owing to possible twisting of the optical fibre bundle and with suppression of the replicas. This effect is obtained by arranging a multimode optical fibre section at the distal end of the single-mode optical fibre bundle.

According to one or more exemplary embodiments, the multimode optical fibre section has a length of between 0.1 mm and 20 mm, advantageously of between 0.1 and 10 mm. The multimode optical fibre section is short enough in this case to be ultra-rigid and long enough to enable jamming of the higher diffraction orders at the output of the single-mode optical fibre bundle.

According to one or more exemplary embodiment, the multimode optical fibre is a step-index fibre enabling jamming of the higher diffraction orders at the output of the single-mode optical fibre bundle over a very short section, of between 0.1 mm and 5 mm for example.

According to one or more exemplary embodiments, the multimode optical fibre is a graded-index fibre requiring a longer wavelength to achieve mode jamming, typically greater than 5 mm.

According to one or more exemplary embodiments, the first light guide comprises a bundle of N single-mode optical fibres formed of a set of individual single-mode optical fibres, each comprising a core and a cladding, typically a hundred to a few tens of thousands of fibres, grouped in the form of a bundle of fibres.

According to one or more exemplary embodiments, the first light guide comprises a bundle of N single-mode optical fibres formed of a set of single-mode cores, preferably at least a hundred. For example, the first light guide is a multi-core fibre and the bundle of N single-mode optical fibres is formed by the single-mode cores of the multi-core fibre.

According to one or more exemplary embodiments, the first light guide is a double-cladded multi-core fibre; a multi-core fibre of this kind offers the advantage of transporting the backscattered light signal highly effectively in the double-clad of multi-core fibre, generally a multimode double-clad.

Single-mode optical fibre signifies a fibre in which light can only propagate in a single mode of the electromagnetic field; by extension, it also means a so-called "effective single-mode" fibre that comprises several modes, but in which the coupling conditions only excite a single mode (generally the fundamental mode) which confines the light throughout propagation (no leakage to the other modes).

In the entire description, the term "single-mode optical fibre" can be used to denote both an individual single-mode optical fibre and a single-mode core of a multi-core fibre.

According to one or more exemplary embodiments, coupling between the single-mode optical fibres of the single-mode optical fibre bundle is less than −20 dB/m, allowing transport and control of the optical beams over a great length of the fibre bundle, while providing the possibility of compensating inter-core phase shift effects.

According to one or more exemplary embodiments, the first spatial light modulator includes a segmented deformable or membrane mirror, for operation in reflection.

According to one or more exemplary embodiments, the first spatial light modulator includes a liquid crystal matrix, for operation in reflection or in transmission.

According to one or more exemplary embodiments, the device for transporting and controlling light beams further comprises an optical system adapted to transport of the light beams emitted by the single-mode optical fibres of the optical fibre bundle to the multimode optical fibre section.

According to one or more exemplary embodiments, the optical system allows optical conjugation between an output facet of the single-mode optical fibre bundle and an input facet of the multimode optical fibre section.

According to one or more exemplary embodiments, an output facet of the single-mode optical fibre bundle and an input facet of the multimode optical fibre section substantially coincide with two focal planes of said optical system.

According to one or more exemplary embodiments, an output facet of the single-mode optical fibre bundle and an input facet of the multimode optical fibre section are fusion-welded and form a mechanical splice.

According to one or more exemplary embodiments, the first light guide comprises a multi-core fibre stretched at a distal end to form a tapered section of decreasing diameter in which the single-mode cores merge to form the multimode fibre section of the second light guide. In this case, the tapered section forms the transition between the single-mode fibre bundle and the multimode fibre section.

According to one or more exemplary embodiments, the device for transporting and controlling light beams is adapted for transporting and controlling light beams comprising optical pulses and additionally includes a device for group delay control of the light pulses in the single-mode optical fibre bundle.

According to a second aspect, the present description relates to an endo-microscopic imaging system comprising a light source; a device according to the first aspect for transporting and controlling the light beams emitted by said source in order to form an illumination beam with a determined phase function; and a detection channel for detecting the light reflected by the object and transmitted through the second light guide and subsequently through the first light guide from their distal end to their proximal end.

According to a third aspect, the present description relates to a method for transporting and controlling light beams for endo-microscopic imaging, without a lens on the distal side, involving:

receiving elementary light beams at a proximal end of a bundle of N single-mode optical fibres of a first light guide, wherein each single-mode optical fibre is intended to receive an elementary light beam and emit a light beam at a distal end, receiving the light beams emitted by all the single-mode optical fibres of the optical fibre bundle via a multimode core of a multimode optical fibre section of a second light guide, arranged at the distal end of the first light guide;

applying a phase shift to each of the elementary beams, by means of at least one first spatial light modular arranged on the side of the proximal end of the first light guide, in order to form an illumination beam with a determined phase function at the distal end of the multimode optical fibre section.

According to one or more exemplary embodiments, the method further comprises a preliminary calibration serving to determine the phase shift to be applied to each of the elementary beams depending on the phase function sought for the illumination beam.

According to one or more exemplary embodiments, the preliminary calibration stage involves partial or total determination of a transmission matrix of the assembly formed by the single-mode optical fibre bundle and the multimode fibre.

According to one or more exemplary embodiments, the purpose of applying the phase shift to each of the elementary beams is to impart a determined phase function to the distal extremity of the multimode optical fibre section in order to form a convergent illumination beam at a given distance from an output facet of the multimode optical fibre section, enabling formation of a focal point.

According to one or more exemplary embodiments, application of successive phase shifts to each of the elementary beams allows scanning of the focal point in a plane at said given distance from the output facet of the multimode optical fibre section and/or at different distances from the output facet of the multimode optical fibre section.

According to one or more exemplary embodiments, the elementary light beams comprise light pulses. The method may then include, according to an exemplary embodiment, group delay control of the light pulses in the single-mode optical fibre bundle.

According to a fourth aspect, the present description relates to an endo-microscopic imaging method without a lens on the distal side, involving:

emission of the light beam;

transport and control of the light beams by means of a method according to the third aspect for illuminating an object by the illumination beam;

detection of the light reflected by the object and transmitted through the second light guide and subsequently through the first light guide, from their distal end to their proximal end.

The nature of the light reflected by the object may be different depending on the application; for example, the light reflected is the backscattered light, or the light emitted, by a fluorescence mechanism for instance.

BRIEF DESCRIPTION OF THE DRAWINGS

Other advantages and characteristics of the invention will appear upon reading the description, illustrated by the figures below.

DETAILED DESCRIPTION

The same references are used to designate identical elements in the figures.

Figure 1A:
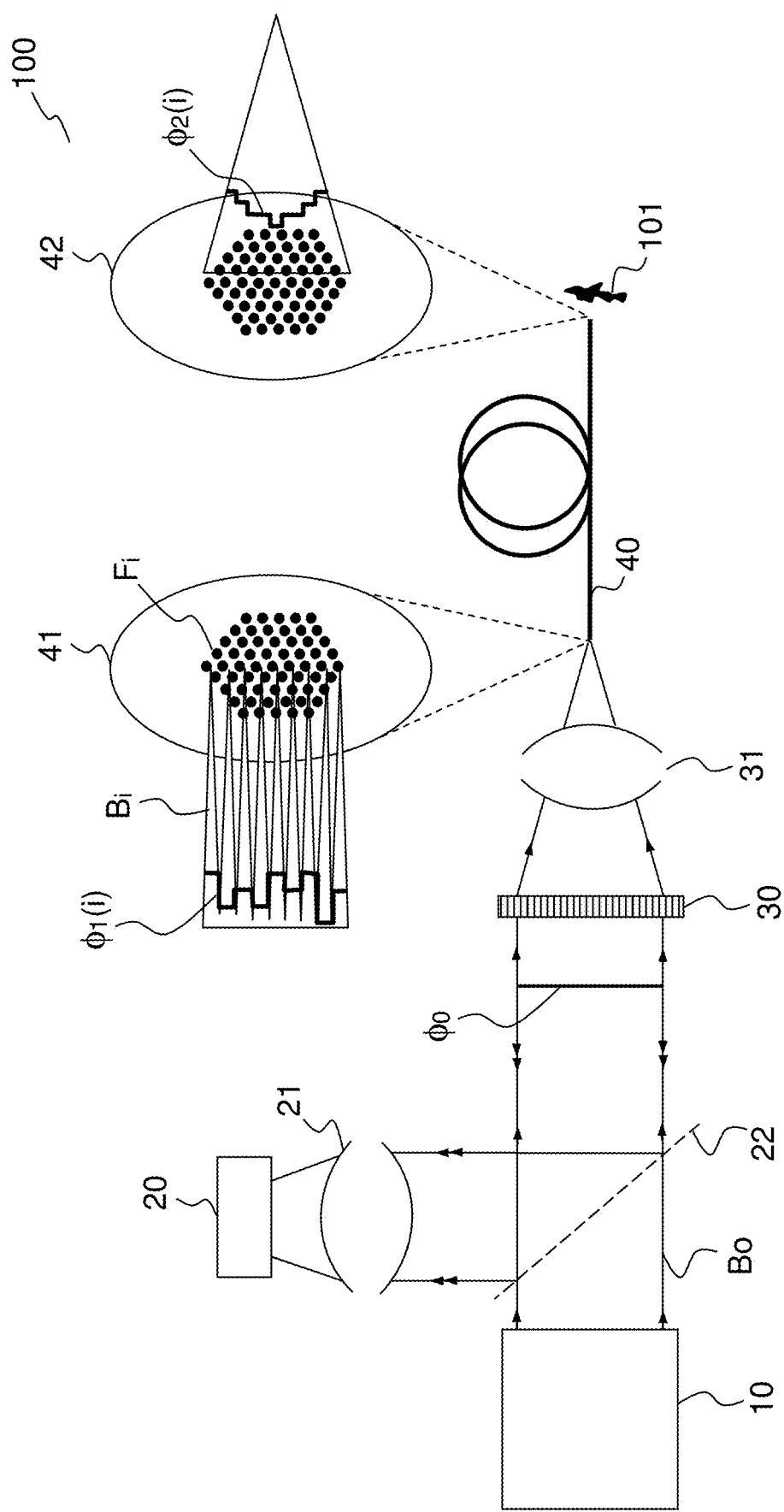
FIGS. 1A to 1C (already described), a block diagram of a so-called "lensless" endoscope according to the prior art, based on use of a single-mode fibre bundle; an image of an example of a multi-core fibre adapted for implementation of an endoscope of the type described in FIG. 1A and an image illustrating the presence of replicas.
Figure 1B:
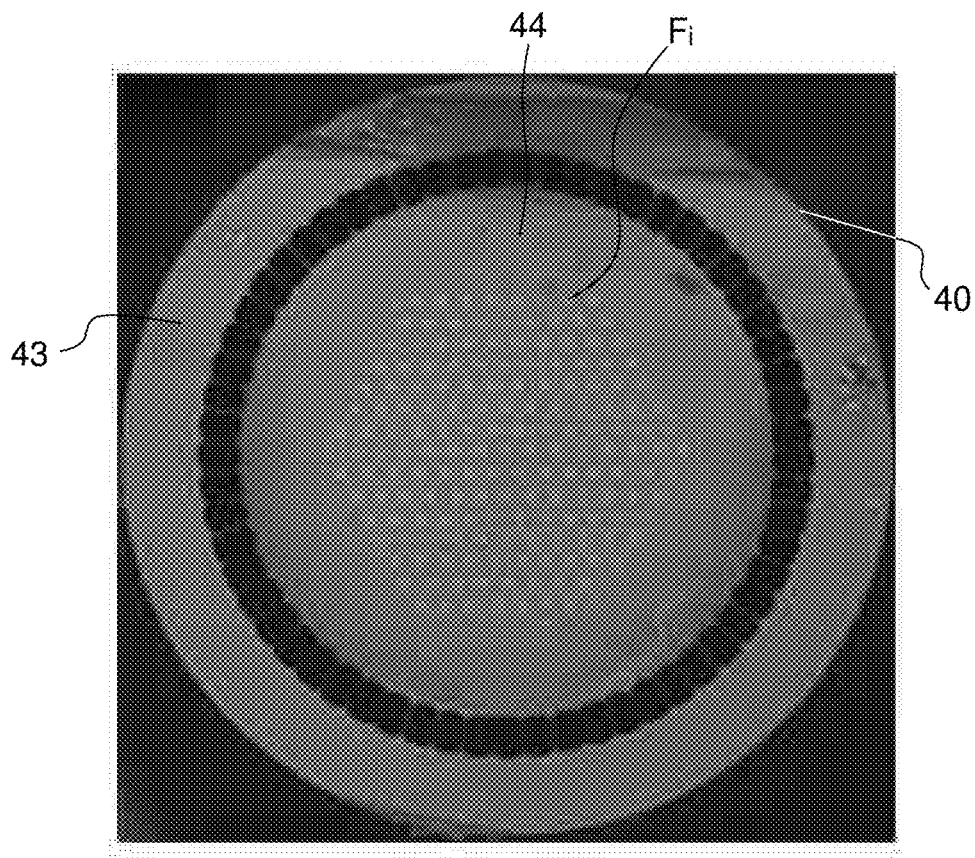
Figure 1C:
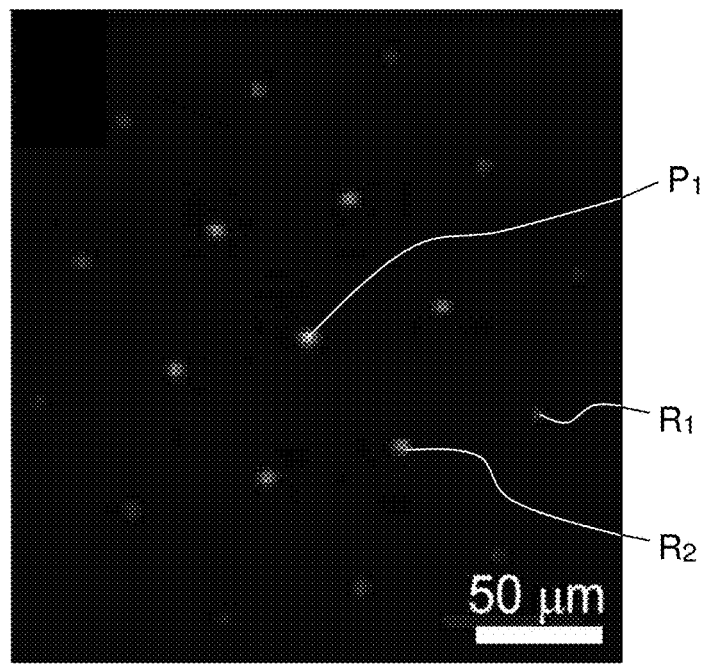
Figure 2:
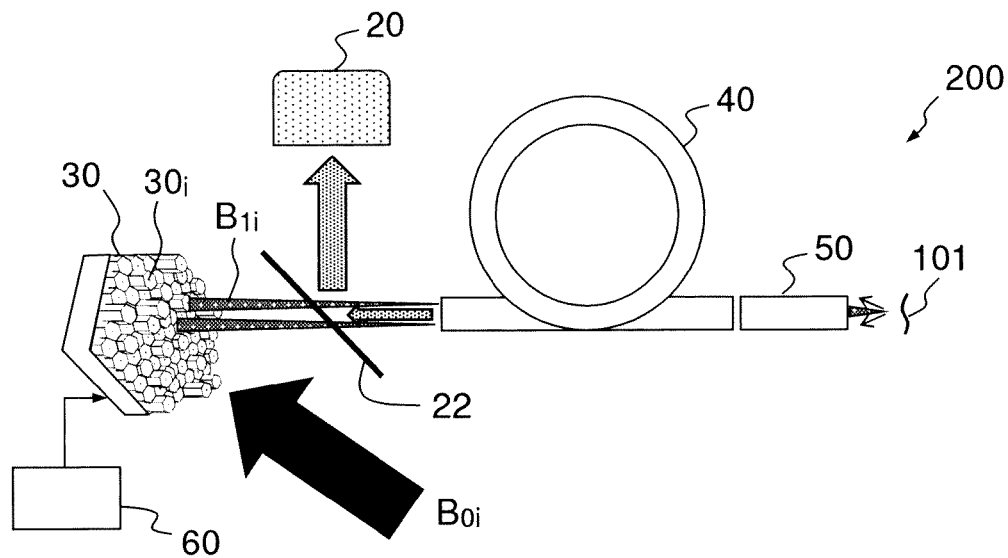
FIG. 2, a block diagram illustrating an example of a lensless endo-microscopic imaging system according to the present description.

FIG. 2 illustrates diagrammatically an example of a "lensless" endo-microscopic imaging system 200 with a device for transporting and controlling light beams according to the present description, adapted for imaging an object bearing the reference 101 in FIG. 2.

The endo-microscopic imaging system 200 comprises a light source (not illustrated in FIG. 2) adapted for emitting light beams $B_{Oi}$, wherein the light beams may include light pulses in the case of application to non-linear imaging. Thus, the light source comprises for example a laser source and, if necessary, an optical system for enlargement and collimation of the light beams emitted.

The endo-microscopic imaging system 200 further comprises a device for transporting and controlling the light beams emitted by said light source in order to illuminate the object 101 according to a selected intensity figures, for example a focal point scanned in the field, or other forms, depending on the applications. The device for transporting and controlling the light beams typically comprises a first light guide 40 with a single-mode optical fibre bundle, a second light guide 50 with a multimode optical fibre section, wherein the second light guide 50 is arranged at the distal end of the first light guide, and an optical device for phase control arranged on the side of the proximal end of the first light guide, comprising in particular a spatial light modulator 30.

The device for transporting and controlling the light beams is said to be "lensless", since it does not have any lens on the distal side, i.e. on the side on which the light beams emerge, with the phase being controlled by the phase control device arranged on the side of a proximal end of the device.

In the rest of the description, it will be simpler to use the term "multimode optical fibre" to refer to the multimode optical fibre section. Furthermore, the second light guide can be formed by the multimode optical fibre section or comprise other elements, for example protective elements, known to those skilled in the art.

The single-mode optical fibre bundle can be formed of set of individual single-mode optical fibres, typically a hundred to a few tens of thousands of fibres, grouped in the form of a bundle of fibres, or may consist of a set of single-mode cores of a multi-core fibre, preferably at least a hundred.

Thus, the first light guide can be formed of the set of individual single-mode optical fibres or comprise other elements, for example protective elements, known to those skilled in the art. The first light guide may also comprise a single-clad or double-clad multi-core fibre and include any other elements useful for producing the guide, such as protective elements, known to those skilled in the art. In the case of a double-clad multi-core fibre, a cladding may be a multimode cladding, adapted to propagate the light flow backscattered by the object.

Advantageously, coupling between the single-mode optical fibres of the single-mode optical fibre bundle is less than −20 dB/m, allowing transport and control of the optical beams over a great length of the fibre bundle, while providing the possibility of compensating inter-core phase shift effects.

The length of the single-mode fibres of the fibre bundle 40 is adapted to the application and more specifically, to the length required for the endomicroscope. Typically, the length of the single-mode fibres of the fibre bundle is between 50 cm and 3 m.

Conversely, the multimode optical fibre section is advantageously selected as short as possible and has for example a length of between 0.1 mm and 20 mm, advantageously of between 0.1 mm and 10 mm. The multimode optical fibre section is short enough in this case to be rigid and long enough to allow jamming of the phase of the propagation modes at the output of the single-mode optical fibre bundle.

The multimode optical fibre may for example be a graded-index fibre or a step-index fibre; in the latter case, jamming of the phase of the propagation modes at the output of the single-mode optical fibre bundle can be achieved by means of a section with a very short length, typically between 0.1 mm and 5 mm.

The multimode optical fibre section can also be intended to form a permanent implant in the case of applications to endoscopic deep brain imaging for example. In the latter case, a longer section of multimode fibre may prove to be of value and consequently use of a graded-index multimode fibre may be appropriate.

The optical phase control device is arranged on the side of the proximal end of the single-mode optical fibre bundle and comprises the spatial light modulator 30 adapted to apply a phase shift to each of the elementary beams $B_{Oi}$, and a control unit 60 for controlling the spatial light modulator allowing application of a phase shift to each of the elementary beams to impart a determined phase function at the distal end of the multimode optical fibre section. The spatial light modulator 30 may for example include a segmented deformable or membrane mirror, for operation in reflection or in transmission.

According to an exemplary embodiment, the imaging system 200 may also comprise means (not illustrated in FIG. 2) of focusing elementary light beams $B_{Oi}$ on elements $30_i$, of the spatial light modulator 30. The means of focusing the elementary light beams $B_{Oi}$, comprise for example a matrix of microlenses or a spatial light modulator, for example a liquid crystal matrix forming a two-dimensional paving of networks having quadratic phases, thus simulating a microlens array.

The endo-microscopic imaging system 200 also comprises a detection channel for detecting the light backscattered by the object 101 and transmitted via the multimode fibre and the single-mode optical fibre bundle from their distal end to their proximal end. In the example in FIG. 2, the detection channel comprises a beam splitter 22, a detector 20 and possibly a lens (not illustrated in FIG. 2) to focus the backscattered light on a detection surface of the detector 20, in addition to a processing unit (not illustrated) for processing the signals derived from the detector 20.

FIGS. 3A to 3D illustrate several examples of arrangement of the single-mode optical fibre and multimode optical fibre bundle, serving to facilitate transport of the light beams emitted by the single-mode optical fibre bundle to the multimode core of the multimode optical fibre.

Figure 3A:
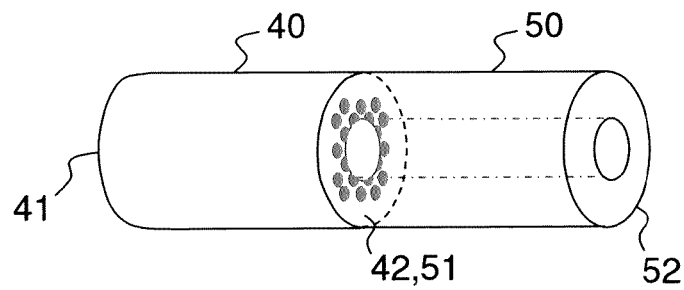
FIGS. 3A to 3D, figures illustrating several examples of arrangement of the single-mode optical fibre bundle and of the multimode optical fibre in a transport and control device according to the present description.

In the example in FIG. 3A, the output facet 42 (or distal facet) of the single-mode optical fibre bundle 40 is maintained in contact with an input facet 51 (or proximal facet) of the multimode optical fibre 50. This involves for example a direct welding between the single-mode optical fibre bundle 40 and the multimode optical fibre 50, or any optical bonding method ensuring good light transmission between the single-mode optical fibres and the multimode fibre.

Figure 3B:
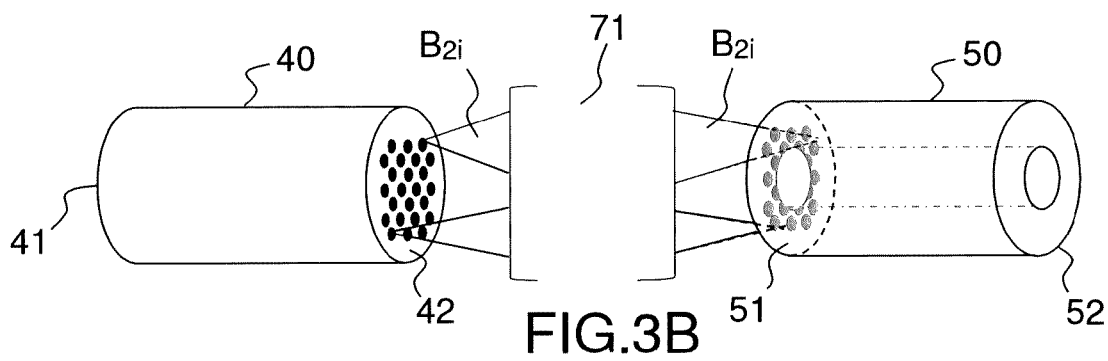
Figure 3C:
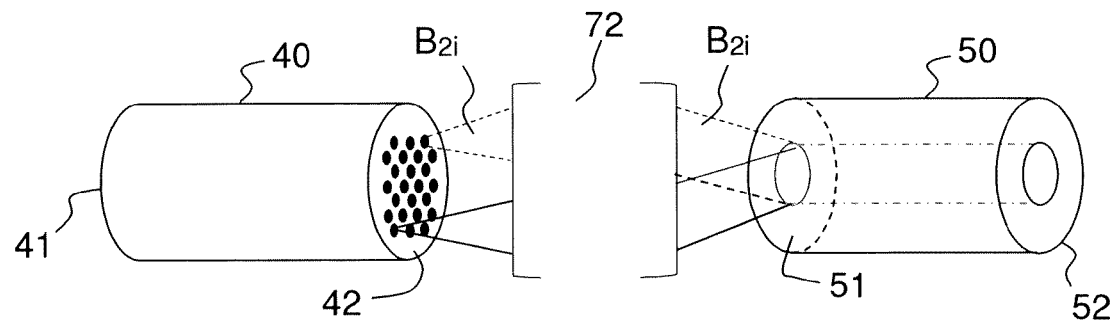

In the examples in FIGS. 3B and 3C, an optical system, respectively referenced 71 and 72 in each of the figures, is arranged between the single-mode optical fibre bundle 40 and the multimode optical fibre for transporting the light beams emitted by the single-mode optical fibres of the optical fibre bundle to the multimode core of the multimode optical fibre section 50.

For example, as illustrated in FIG. 3B, the optical system 71 allows optical conjugation between an output facet 42 of the single-mode optical fibre bundle and an input facet 51 of the multimode optical fibre section.

According to another example, as illustrated in FIG. 3C, the output facet 42 of the single-mode optical fibre bundle and the input facet 51 of the multimode optical fibre section substantially coincide with two focal planes of the optical system 72.

In both these cases, adjustment of the optical system 71 or the optical system 72 does not need to be perfect, the aim being to facilitate transport of the light beams emitted by the single-mode optical fibres of the optical fibre bundle towards the multimode core of the multimode optical fibre section.

Figure 3D:
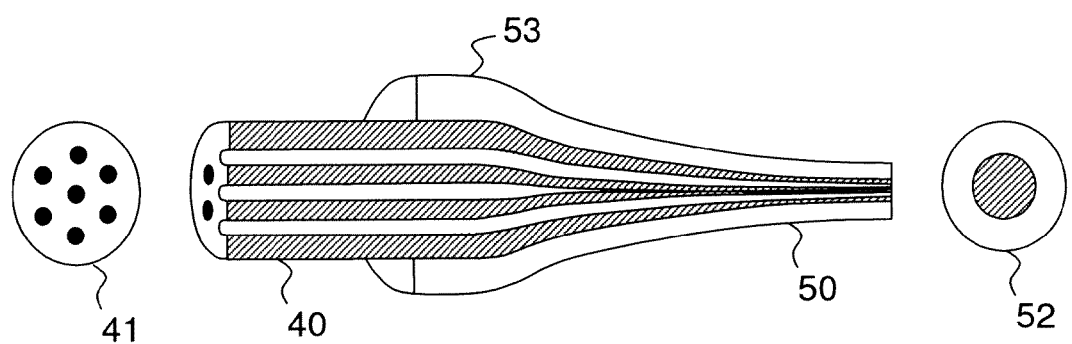

FIG. 3D shows a particular example in which the first light guide includes a multi-core fibre 40 tapered at a distal end to form a tapered section of decreasing diameter. In this tapered section in which the single-mode cores merge, propagation becomes multimode, as described in the article by T. A. Birks et al. ("The photonic lantern", Advances in Optics and Photonics 7, 107-167 (2015)); the multimode fibre section 50 of the second light guide is obtained in this manner. In this case, the tapered section forms the transition between the single-mode fibre bundle 40 and the multimode fibre section 50. The assembly has a common cladding 53.

Figure 4A:
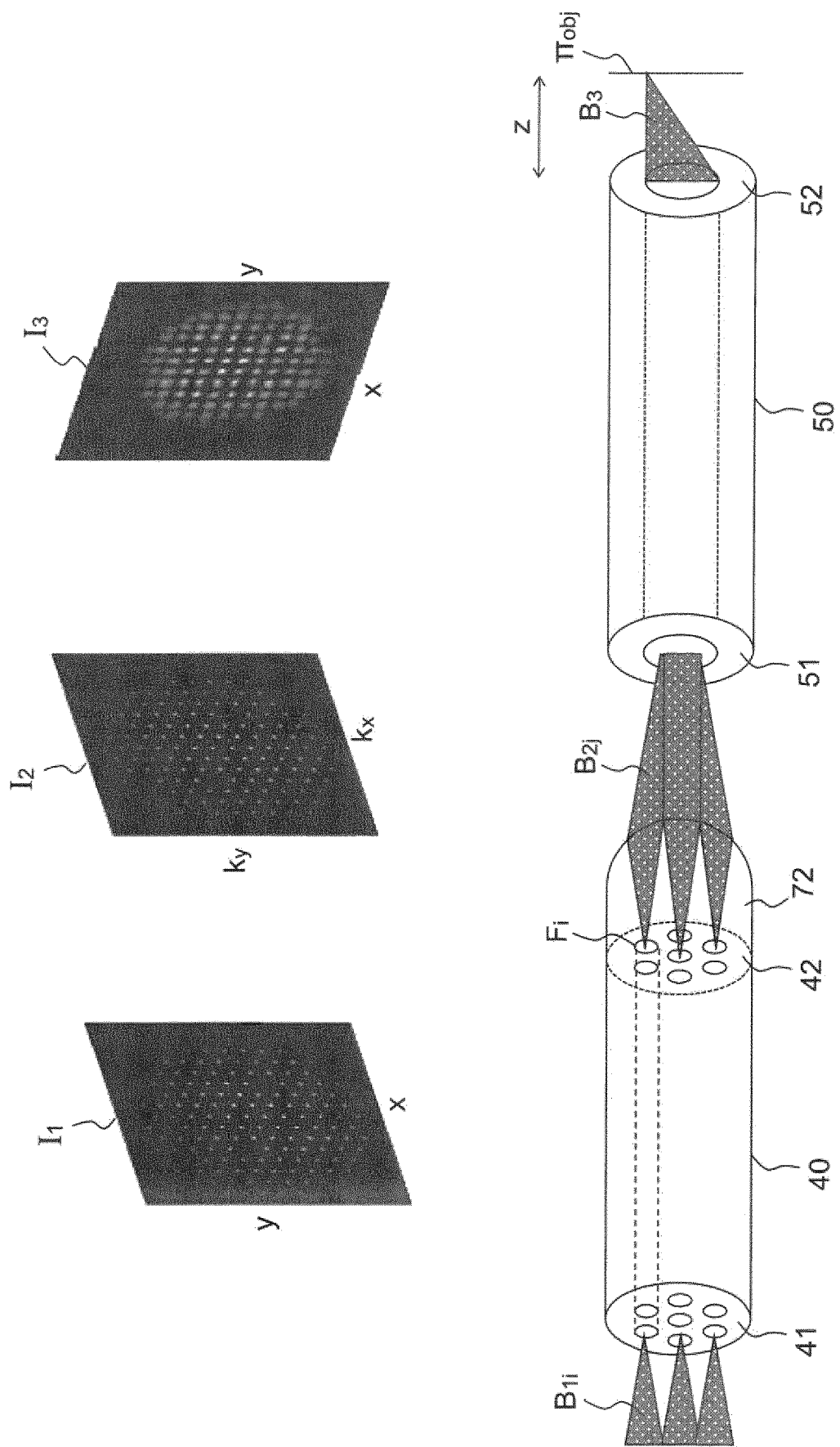
FIGS. 4A to 4C, diagrams illustrating stages of an example of a method for transporting and controlling light beams according to the present description.
Figure 4B:
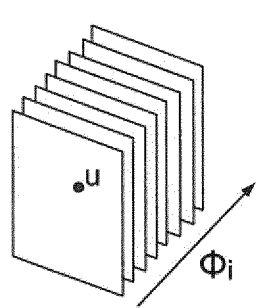
Figure 4C:
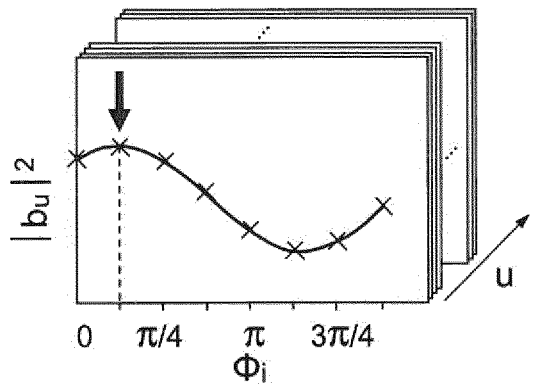

FIG. 4A illustrates in greater detail the stages of an example of a method for transporting and controlling the light beams according to the present description and FIGS. 4B and 4C stages of an example of preliminary calibration.

In the example chosen in order to illustrate the method of transporting and controlling the light beams, an optical system 72, for example a lens, serves to transport the light beams emitted by the single-mode optical fibres of the optical fibre bundle 40 to the multimode optical fibre bundle 50, as illustrated for example in FIG. 3C. In this example, the output facet 42 of the single-mode optical fibre bundle and the input facet 51 of the multimode optical fibre section substantially coincide with two focal planes or "Fourier planes" of the optical system 72.

As illustrated in FIG. 4A, elementary light beams $B_{1i}$, the phase of which can be controlled by means of the spatial light modulator 30 (not illustrated in FIG. 4A), are sent to each of the single-mode fibres $F_i$ of the fibre bundle 40. Each single-mode fibre $F_i$, subsequently emits a light beam $B_{2i}$ resulting from transmission of the light beam $B_{1i}$ via the single-mode fibre $F_i$. The set of light beams $B_{2i}$ is identified in real space (x,y) on the output facet 42 of the single-mode optical fibre bundle 40 to form a set N of discrete input modes i, each associated with a fibre $F_i$, the intensities of which are illustrated in the image $I_1$ in FIG. 4A. Given that the output facet 42 of the single-mode optical fibre bundle and the output facet 51 of the multimode optical fibre section are in Fourier planes of the optical system 72, each input mode i identified by its real coordinate $(x_i, y_i)$ has a corresponding intermediate mode j identified by an input direction $(kx_j, ky_j)$ in the plane of the input facet of the multimode fibre 50. The intensities of the N intermediate modes j are illustrated in image $I_2$ in FIG. 4A. The multimode fibre is characterised by a finite number of own eigenmodes. In practice, N superpositions (or linear combinations) of eigenmodes are addressed, whereby N corresponds to the number of single-mode fibres indexed by i, each superposition consisting of a subset of the eigenmodes of the multimode fibre.

The distribution of the electromagnetic field at the output of the multimode fibre 50 is known as output mode u. By means of the method according to the present description, it is attempted to form the output mode u allowing formation of the illumination beam having the desired phase function and/or associated intensity function at the output of the multimode core of the multimode fibre section 50.

As illustrated in FIG. 4A for example, the phase function is determined to form a converging beam $B_3$ in order to form a focal point in a plane situated at a distance z from the output facet 52 of the multimode fibre section 50. The image $I_3$ in FIG. 4A shows output mode intensities u corresponding to different focal points that can be addressed successively during a scan.

Other forms of illumination beams can be sought depending on the application. In the case of brain imaging for example, an illumination beam may for example be sought, the shape of which corresponds to that of the elements (neurons) that one wishes to visualise.

Knowledge of the phase shifts to be applied to the light beams $B_{1i}$, is derived from a preliminary characterisation of the single-mode optical fibre bundle and the multimode fibre section.

It is for example possible to determine experimentally a complete or partial complex transmission matrix of the assembly formed by the single-mode optical fibre bundle and the multimode fibre section. A complex transmission matrix of an optical system generally expresses the amplitude and phase of the light field in a given plane at the output of the optical system as a function of the amplitude and the phase of the light field in a plane at the input of the optical system. Through knowledge of the transmission matrix, it is possible to characterise the system formed by the single-mode optical fibre bundle and the multimode fibre section assembly in order to determine the phase shift to be applied to each of the elementary light beams $B_{1i}$.

Thus, a complex transmission matrix $K_i^u$ can be defined, with an amplitude $A_i^u$ and a phase $P_i^u$:

$$K_i^u = A_i^u e^{iP_i^u}$$

In practice, determination of the matrix $K_i^u$ may be partial and may be limited for example to determination of the matrix $P_i^u$ that essentially governs intensity distribution in the plane of the object (with the amplitude $A_i^u$ playing a marginal role). It is likewise possible to determine the matrix $K_i^u$ incompletely, but this may result in less accuracy in the desired phase function for the illumination beam.

In order to determine the matrix $K_i^u$ of the assembly formed by the single-mode optical fibre bundle and the multimode fibre section, interference methods based on measurements of the interference between the light wave at the multimode optical fibre output and a reference wave can be used. The interference figure is analysed for successive phase shifts applied to each of the elementary fibres or, equivalently, to the reference, allowing determination of the matrix $K_i^u$. This type of method is described for example in the article by Cizmar et al. in which it is sought to determine the transmission matrix of a multimode optical fibre (see '*Shaping the light transmission through a multimode optical fibre: complex transformation analysis and applications in biophotonics*' Opt Express 19, 18871-18884 (2011)).

Once the transmission matrix $K_i^u$ has been determined, it can be recorded in the control unit 60 of the spatial light modulator 30, so that a preliminary calibration is not necessary for each implementation of the imaging method. Alternatively, a new calibration can be performed before starting a further imaging process.

FIGS. 4B and 4C illustrate a stage of preliminary calibration of the method of transporting and controlling the light beams according to the present description, based on characterisation of the system formed by the single-mode optical fibre bundle and the multimode fibre section and specifically adapted to formation of a focal point, whether scanned or not.

In this example, it is assumed that one is seeking to form focal points at different points in the plane $\Pi_{obj}$ positioned at a distance z from the output facet 52 of the multimode optical fibre, as illustrated in FIG. 4A. Each focal point corresponds to a converging beam $B_3^k$. In practice, it will be attempted for example to scan a predetermined object field and thus vary the phase shifts applied to the elementary light beams $B_{1i}$, by means of the spatial light modulator 30 in order to obtain the desired scanning of the object field.

For calibration, a matrix detector, for example a camera, is arranged in the plane of the object $\Pi_{obj}$ or in a conjugate plane. Each pixel of the camera has an "output mode" referenced u. The number of output modes u therefore corresponds in this example to the number M of camera pixels. It is sought to determine the phases $\Phi_i$ to be applied to the elementary light beams $B_{1i}$, in order to achieve maximum intensity of each output mode u.

More specifically, a complex transmission matrix $K_i^u$ can be determined linking the N input modes i and the M output modes u:

$$B_3^{u=1,M} = K_i^u B_1^{i=1,N}$$

The number N of input modes is limited by the number of single-mode optical fibres in the fibre bundle 40 and the number M of output modes is limited by the number of camera pixels.

As explained above, the complex transmission matrix $K_i^u$ can be defined, with an amplitude $A_i^u$ and a phase $P_i^u$:

$$K_i^u = A_i^u e^{i P_i^u}$$

In practice, determination of the matrix $K_i^u$ is solely a matter of measuring the matrix $P_i^u$ that essentially controls the intensity distribution in the plane of the object.

Determination of the matrix $P_i^u$ may comprise the following stages:

Sending two input modes: a reference mode i=0 and an input mode i to which a phase $\Phi_i$ is added;

Recording for each output mode u, i.e. for each camera pixel, the resulting intensity for a given number of intensity values equidistant from $\Phi_i$, for example 8, between 0 and $2\pi$, as shown in FIG. 4C;

Recording for each output mode u of the phase $\Phi_i$ which achieves maximum intensity (FIG. 4B);

Reiteration for each input mode i.

The stages of calibrating the method of transporting and controlling the light beams described above may of course also be applied when the single-mode optical fibre bundle 40 and the multimode fibre section 50 are arranged differently.

In particular, if the input facet 51 is in the same plane, or in a conjugate plane with the output facet 42 of the single-mode fibre bundle 40, the intermediate facet associated with the input facet 51 of the multimode fibre 50 may be indexed in real space (x, y).

Figure 5:
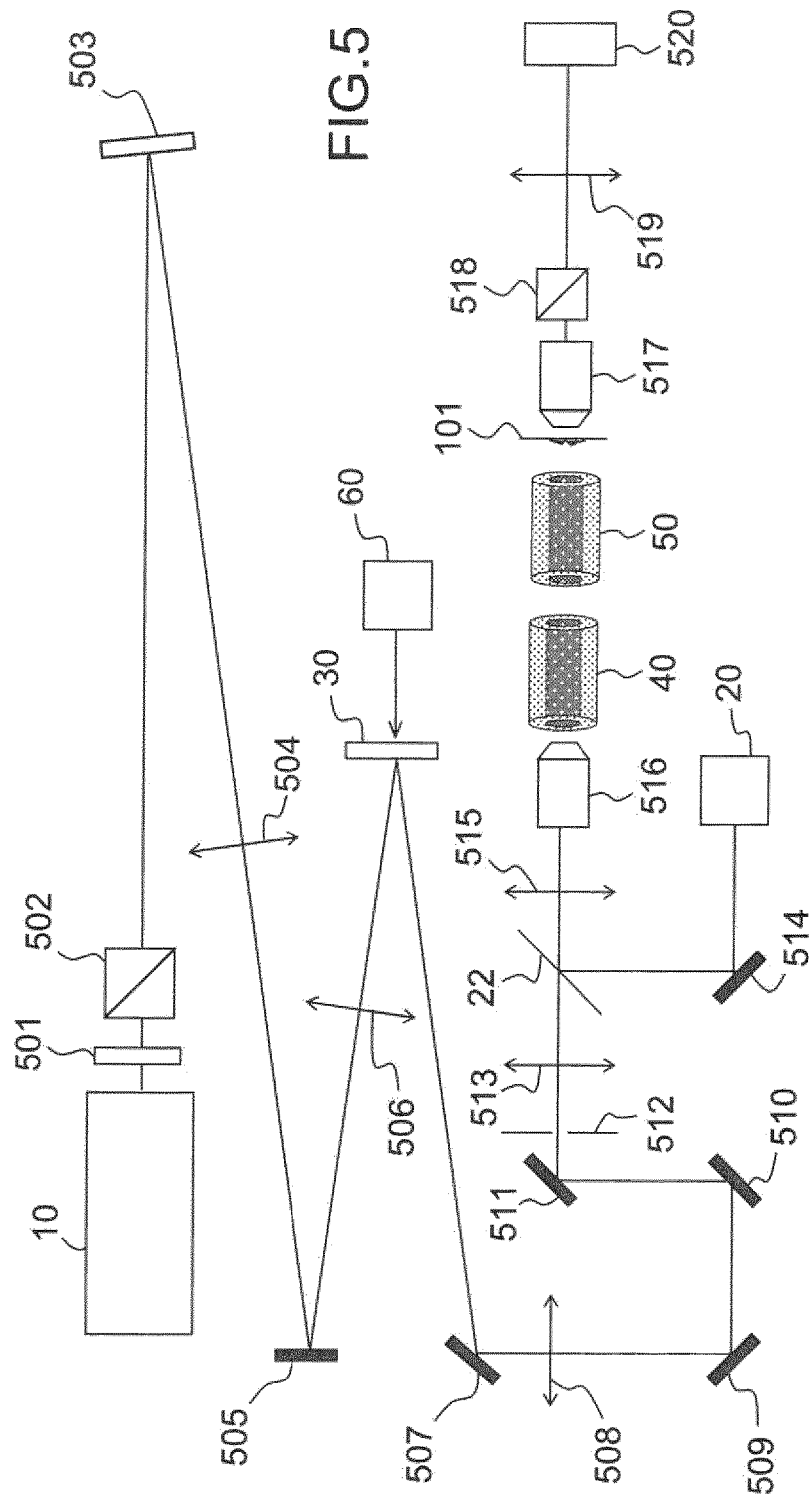
FIG. 5, a diagram illustrating an example of an experimental assembly for validating a method of transporting and controlling light beams according to the present description.

FIG. 5, shows an example of experimental assembly implemented for validating a method of transporting and controlling light beams according to the present description.

The experimental assembly comprises a laser source 10 emitting a light beam sent on a "wavefront shaper" 503, for example a microlens array or a two-dimensional spatial light modulator drawing a network of quadratic phases simulating a microlens array and forming a set of elementary beams focused on the segments of a segmented deformable mirror 30. A telescope 504, 506 is used to adjust the dimensions of the beam in the plane of the deformable mirror 30. Each segment of the deformable mirror 30 is imaged on a single mode fibre of the single-mode optical fibre bundle 40 (imager 508, 513, 515, 516). A control device 60 for controlling the deformable mirror 30 serves to control the phase $\Phi_i$ associated with each input mode i and corresponding to each of the elementary beams. A lens with a focal length of f=500 µm (not visible in FIG. 5) is positioned on the output facet of the fibre bundle 40 such that the output facet of the fibre bundle 40 and the input facet of the multimode fibre 50 are in Fourier planes. The intensity distribution in the plane of the object 101 is observed using a CMOS camera 520 comprising M=4096 pixels and conjugated with the plane of the object 101 by means of a lens 517. The assembly formed of a half-wave plate 501 and a polariser 502 allows adjustment of the polarisation state so that it coincides with the state for which the wavefront shaper 503 is active in the event that this component uses liquid crystals; furthermore, this assembly allows adjustment of the power sent to the sample 101. A polariser 518 allows selection of a single polarisation state for which the transmission matrix is measured and the focal point in the optimised plane $\Pi_{obj}$. A beam splitter 22 is used to reflect towards a detector 20 the light backscattered or emitted (in the case of fluorescence) by the object and transmitted from the distal side to the proximal side by the multimode fibre section and the first light guide. The detector 20 is for example a photomultiplier or an avalanche photodiode. When the sample 101 is scanned with focused beam, the signal backscattered or emitted by each point of the sample is collected by means of the detector 101 to form an image.

Figure 6A:
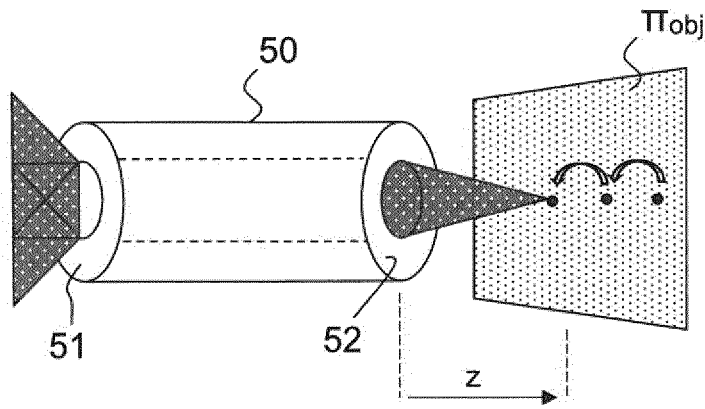
FIGS. 6A to 6C, respectively a block diagram of experimental validation performed using the assembly in FIG. 5 and the images obtained.

A calibration of the method of transporting and controlling the light beams implemented using the experimental assembly in FIG. 5 was also performed in order to check the position of a focal point in the field of the object $\Pi_{obj}$ as illustrated in the diagram in FIG. 6A. The calibration is performed according to the protocol for determining the transmission matrix described above.

In the example shown in FIG. 6A, the plane of the object is located at a distance z=250 µm from the output facet of the multimode fibre section.

Figure 6B:
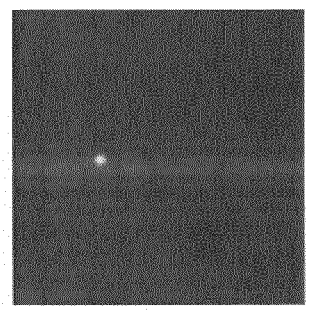
Figure 6C:
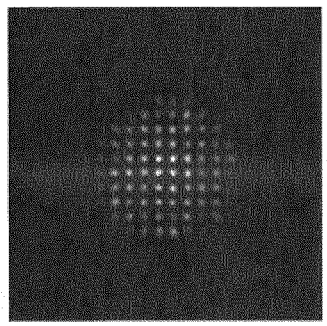

In FIG. 6B, a focal point in the plane of the object obtained by means of the device shown in FIG. 5 is observed. As can be seen, no replica is visible. FIG. 6C represents a subassembly of focal points corresponding to different output modes u obtained by applying phases $\Phi_i$ to the elementary light beams $B_{1i}$. In practice, a single focal point is visible as shown in FIG. 6B; FIG. 6C shows several points in order to appreciate the field of view.

Thus, the applicants have shown both theoretically and experimentally that after a very short propagation distance in the core of the multimode fibre, typically 1 mm or a few millimetres depending on the type of fibre, the propagation modes display random phases. This random nature of the phases associated with each propagation mode of the multimode fibre is at the very origin of disappearance of the replicas. Since the relative phase shifts between the modes of the multimode fibre result from the propagation, it will be understood why a step-index multimode fibre is more effective than a graded-index multimode fibre in jamming the modes; indeed, in a step-index fibre, the propagation constants associated with each of the modes are more dispersed, resulting in larger differential phase shifts.

Although the phases accumulated by the different modes during propagation in the multimode fibre are ultimately random, they are however deterministic and are included in determination of the transmission matrix encompassing the first light guide and the multimode optical fibre.

The applicants have thus demonstrated the feasibility of a device for transporting and controlling light beams for lensless endo-microscopy, wherein a function of scanning the field of the object at a given distance z from the output facet 52 of the multimode optical fibre section 50 can be obtained by controlling the phase shifts applied by means of the spatial light modulator 30.

The device for transporting and controlling light beams according to the present description also allows selection of the distance z from the plane of the object. For this purpose, a calibration as described above can be performed for a set of values z of the distance between the plane of the object and the output facet 52 of the multimode optical fibre section.

Figure 7:
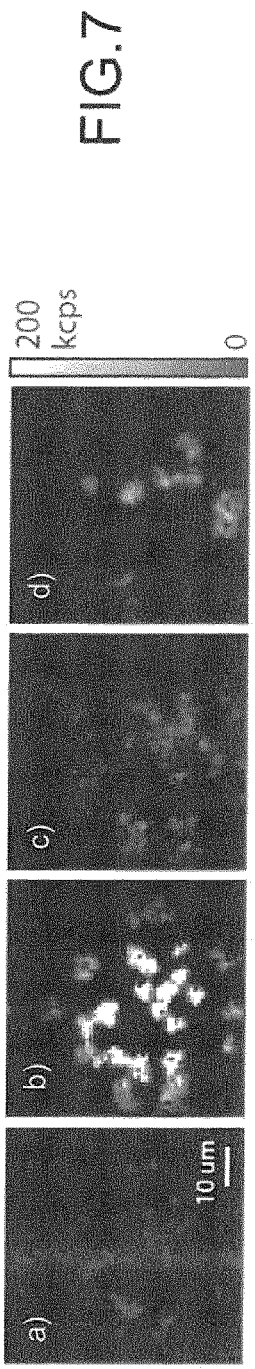
FIG. 7, images obtained using the experimental assembly in FIG. 5.

FIG. 7 thus shows images of fluorescent beads obtained by means of the experimental assembly in FIG. 5 and detected by the detector 20 for z values equal to z=10 μm (a), z=40 μm (b), z=70 μm (c), z=100 μm (d).

More specifically, the light source used to obtain these images is a Titanium:Sapphire laser at 800 nm emitting pulses of 200 fs; the images obtained are two-photon images and the detector 20 is an avalanche photodiode.

These experimental results therefore also demonstrate the application of the method of transporting and controlling light beams in non-linear imaging, since the device is suitable for transmission of short pulses.

However, when handling ultra-short pulses, the device for transporting and controlling light beams according to the present description may also comprise a group delay control device for the light pulses in the single-mode optical fibre bundle, as described in the publication by E. R. Andresen et al. ("Measurement and compensation of residual group delay in a multi-core fibre for lensless endoscopy", JOSA B, Vol. 32, No. 6, 1221-1228 (2015)).

It is therefore possible to perform lensless endo-microscopic imaging by means of the method described. Apart from transporting and controlling the light beams by means of the method previously described, the endo-microscopic imaging method may also comprise detection of the light backscattered by the object and transmitted via the multimode fibre and the single-mode optical fibre bundle from their distal end to their proximal end.

Although described though a number of detailed exemplary embodiments, the device for transporting and controlling light pulses for so-called "lensless" endo-microscopic imaging, in addition to the lensless endo-microscopic systems and methods comprise different alternative embodiments, modifications and improvements which will be obvious to those skilled in the art, its being understood that these different alternative embodiments, modifications and improvements fall within the scope of the invention as defined in the following claims.

The invention claimed is:

1. A device for transporting and controlling light beams for endo-microscopic imaging, comprising:
   a first light guide comprising a single-mode optical fibre bundle, wherein each single-mode optical fibre is intended to receive an elementary light beam at a proximal end and emit a light beam at a distal end,
   a second light guide comprising a multimode optical fibre section, arranged at the distal end of the first light guide, wherein said multimode optical fibre is a step-index fibre, wherein the multimode optical fibre section is intended to receive the light beams emitted by the single-mode optical fibres of the single-mode optical fibre bundle, and wherein no lens is located at the distal end of the first light guide;
   an optical device for phase control arranged on the side of the proximal end of the first light guide comprising:
      at least one spatial light modulator adapted to apply a phase shift to each of the elementary beams;
      means of programming the first spatial light modulator allowing application of a phase shift to each of the elementary beams in order to form an illumination beam with a determined phase function at the distal end of the multimode optical fibre.

2. The device for transporting and controlling light pulses according to claim 1, wherein the multimode optical fibre section has a length of between 0.1 mm and 20 mm.

3. The device for transporting and controlling light beams according to claim 1, further comprising an optical system adapted to transport of the light beams emitted by the single-mode optical fibres of the optical fibre bundle to the multimode optical fibre section.

4. The device for transporting and controlling light beams according to claim 1, wherein the first light guide comprises a double-clad multi-core fibre.

5. A endo-microscopic imaging system comprising:
   a light source for emitting light beams;
   a device according to claim 1 for transporting and controlling the light beams emitted by said source for forming an illumination beam for illuminating an object with a determined phase function; and
   a detection channel designed to detect the light reflected by the object and transmitted through the second light guide and subsequently through the first light guide, from their distal end to their proximal end.

6. A method for transporting and controlling light beams for endo-microscopic imaging, comprising:
   receiving elementary light beams at a proximal end of a bundle of N single-mode optical fibres of a first light guide, wherein each single-mode optical fibre is intended to receive an elementary light beam and emit a light beam at a distal end,
   receiving the light beams emitted by all the single-mode optical fibres of the optical fibre bundle via a multimode core of a multimode optical fibre section of a second light guide, arranged at the distal end of the first light guide, wherein said multimode optical fibre is a step-index fibre, and wherein no lens is located at the distal end of the first light guide;
   applying a phase shift to each of the elementary beams, by means of at least one first spatial light modulator arranged on the side of the proximal end of the first light guide, in order to form an illumination beam with a determined phase function at the distal end of the multimode optical fibre section.

7. The method according to claim 6, further comprising a preliminary calibration serving to determine the phase shift to be applied to each of the elementary beams depending on the phase function sought for the illumination beam.

8. The method according to claim 6, wherein application of the phase shift to each of the elementary beams aims to form at the distal end of the multimode optical fibre section a convergent illumination beam at a given distance from an output facet of the multimode optical fibre section, enabling formation of a focal point.

9. The method according to claim 8, wherein application of successive phase shifts to each of the elementary beams allows scanning of said focal point in a plane at said given distance from the output facet of the multimode optical fibre section and/or at different distances from the output facet of the multimode optical fibre section.

10. The method for endo-microscopic imaging without a lens on the distal side, comprising:
   emission of the light beam;
   transport and control of the light beams by means of a method as described according to claim 6 for illuminating an object by the illumination beam;
   detection of the light reflected by the object and transmitted through the second light guide and subsequently through the first light guide, from their distal end to their proximal end.

* * * * *